(12) United States Patent
Horstman et al.

(10) Patent No.: US 7,858,697 B2
(45) Date of Patent: *Dec. 28, 2010

(54) CARBINOL FUNCTIONAL SILICONE RESINS

(75) Inventors: John Bernard Horstman, Midland, MI (US); Donald Liles, Midland, MI (US); Randall Schmidt, Midland, MI (US); Gary Wieber, Midland, MI (US); Gerald Lawrence Witucki, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 805 days.

This patent is subject to a terminal disclaimer.

(21) Appl. No.: 10/568,512

(22) PCT Filed: Oct. 8, 2004

(86) PCT No.: PCT/US2004/033189

§ 371 (c)(1),
(2), (4) Date: Feb. 15, 2006

(87) PCT Pub. No.: WO2005/037891

PCT Pub. Date: Apr. 28, 2005

(65) Prior Publication Data

US 2006/0235142 A1 Oct. 19, 2006

Related U.S. Application Data

(60) Provisional application No. 60/510,247, filed on Oct. 10, 2003.

(51) Int. Cl.
C08L 83/04 (2006.01)
C08G 77/04 (2006.01)

(52) U.S. Cl. .................................. 524/588; 528/33

(58) Field of Classification Search ........................ None
See application file for complete search history.

(56) References Cited

U.S. PATENT DOCUMENTS

| | | | | |
|---|---|---|---|---|
| 3,410,820 A | * | 11/1968 | Harrod | 524/860 |
| 4,032,502 A | * | 6/1977 | Lee et al. | 523/212 |
| 4,125,510 A | | 11/1978 | Antonen | |
| 4,157,357 A | | 6/1979 | Mine et al. | |
| 4,202,807 A | | 5/1980 | Moretto et al. | |
| 4,234,697 A | | 11/1980 | Homan et al. | |
| 4,614,675 A | * | 9/1986 | Ona et al. | 427/387 |
| 4,657,986 A | | 4/1987 | Isayama et al. | |
| 4,684,534 A | | 8/1987 | Valentine | |
| 4,722,951 A | | 2/1988 | Yoshioka et al. | |
| 4,795,680 A | | 1/1989 | Rich et al. | |
| 4,822,716 A | * | 4/1989 | Onishi et al. | 430/192 |
| 4,877,822 A | | 10/1989 | Itoh et al. | |
| 4,952,657 A | * | 8/1990 | Riding et al. | 528/27 |
| 5,013,577 A | | 5/1991 | Wright et al. | |
| 5,102,960 A | | 4/1992 | Imai et al. | |
| 5,106,611 A | * | 4/1992 | Forestier et al. | 424/47 |
| 5,126,126 A | | 6/1992 | Varaprath et al. | |
| 5,135,993 A | | 8/1992 | Decker et al. | |
| 5,152,984 A | | 10/1992 | Varaprath et al. | |
| 5,158,854 A | * | 10/1992 | Imamura et al. | 430/192 |
| 5,162,389 A | * | 11/1992 | Lee et al. | 522/42 |
| 5,262,507 A | | 11/1993 | Decker et al. | |
| 5,264,319 A | * | 11/1993 | Sugiyama et al. | 430/192 |
| 5,279,921 A | * | 1/1994 | Onishi et al. | 430/270.1 |
| 5,283,279 A | | 2/1994 | Hara et al. | |
| 5,290,882 A | | 3/1994 | Shiobara et al. | |
| 5,290,901 A | | 3/1994 | Burns et al. | |
| 5,362,821 A | | 11/1994 | Decker et al. | |
| 5,362,833 A | * | 11/1994 | Chen et al. | 528/25 |
| 5,378,532 A | | 1/1995 | Decker et al. | |
| 5,378,789 A | * | 1/1995 | Raleigh et al. | 528/29 |
| 5,405,688 A | | 4/1995 | Decker et al. | |
| 5,431,765 A | | 7/1995 | Decker et al. | |
| 5,516,858 A | | 5/1996 | Morita et al. | |
| 5,637,667 A | * | 6/1997 | Shimozawa et al. | 528/25 |
| 5,731,126 A | * | 3/1998 | Takemura et al. | 430/270.1 |
| 5,814,679 A | | 9/1998 | Eckberg et al. | |
| 5,840,806 A | | 11/1998 | Komazaki et al. | |
| 5,891,969 A | | 4/1999 | Mine et al. | |
| 5,916,992 A | | 6/1999 | Wilt et al. | |
| 5,939,491 A | | 8/1999 | Wilt et al. | |
| 5,952,439 A | | 9/1999 | Morita et al. | |
| 6,071,990 A | | 6/2000 | Yip et al. | |
| 6,087,064 A | * | 7/2000 | Lin et al. | 430/270.1 |
| 6,297,331 B1 | | 10/2001 | Langenhagen et al. | |
| 6,593,417 B1 | | 7/2003 | Anderson et al. | |
| 6,610,777 B1 | | 8/2003 | Anderson et al. | |
| 6,806,509 B2 | * | 10/2004 | Yoshino et al. | 257/103 |

* cited by examiner

Primary Examiner—Randy Gulakowski
Assistant Examiner—Robert Loewe
(74) Attorney, Agent, or Firm—Patricia M. Scaduto

(57) ABSTRACT

This invention relates to carbinol-functional silicone resins and a method to manufacture carbinol-functional silicone resins. This invention also relates to emulsion compositions comprising the carbinol-functional silicone resins. The carbinol-functional silicone resins can be used to make tough, water resistant, solvent resistant, scratch resistant, and heat resistant materials by formulating and reacting these silicone resins with certain organic materials.

19 Claims, No Drawings

CARBINOL FUNCTIONAL SILICONE RESINS

CROSS REFERENCE TO RELATED APPLICATIONS

This application is a U.S. national stage filing under 35 U.S.C. §371 of PCT Application No. PCT/US2004/033189 filed on 8 Oct. 2004, currently pending, which claims the benefit of U.S. Provisional Patent Application No. 60/510,247 filed 10 Oct. 2003 under 35 U.S.C. §119 (e). PCT Application No. PCT/US2004/033189 and U.S. Provisional Patent Application No. 60/510,247 are hereby incorporated by reference.

This invention relates to carbinol-functional silicone resins and a method to manufacture carbinol-functional silicone resins. The carbinol-functional silicone resins can be used to make tough, water resistant, solvent resistant, scratch resistant, and heat resistant materials by formulating and reacting these silicone resins with certain organic materials. Methods to make carbinol-functional silicone resins have been described in the art. For example, in U.S. Pat. No. 5,290,901 is disclosed a method for the preparation of carbinol-functional organosiloxanes and carbinol-functional organosiloxane resins. The method comprises contacting a cyclic silyl ether with an organosiloxane or an organosiloxane resin at a temperature within a range of about 25° C. to 150° C. The method may be conducted in the presence of an inert organic solvent to facilitate dissolution and contact of the reactants. Also disclosed in the '901 patent is a method for preparation of carbinol-functional organosiloxane resins described by formula $(SiO_2)_w(RSiO_{3/2})_x(R_2SiO)_y(R_3SiO_2)_z\{O_2SiR_2(CR^1{}_2)_b OH\}_a$, the method comprising: contacting a cyclic silyl ether described by formula

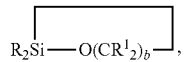

with an organosiloxane resin described by formula $(SiO_2)_w(RSiO_{3/2})_x(R_2SiO)_y(R_3SiO_2)_z$ at a temperature within a range of about 25° C. to 150° C. where each R is independently selected from a group consisting of alkyls comprising one to 20 carbon atoms, cycloalkyls comprising three to 20 carbon atoms, alkenyls comprising two to 20 carbon atoms, aralkyls, and aryls; each R.sup.1 is independently selected from a group consisting of hydrogen, R, and substituted hydrocarbyls comprising one to 20 carbon atoms; b=3, 4, or 5; the values w, x, y, z are mole percents, w<100, w+x>0, and w+x+y+z=100:the organosiloxane resin comprises greater than zero weight percent silanol to about 30 weight percent silanol, and the value a represents the percent of the silanol substituted with carbinol-functional silyl and a>0.

In U.S. Pat. No. 5,814,679 is disclosed carbinol functionalized silicones which lowers the release forces of epoxy silicone photo-curable release compositions, by co-photocuring with the epoxy functionalized silicone. The '679 patent further discloses that photo-curable silicone compositions with long chain silicone compounds that contain carbinol-functionalities co-polymerize or co-cure with epoxy functional photo curable silicones thereby permitting the formulation of premium release photo-curable silicone compositions.

In U.S. Pat. No. 6,297,331 is disclosed organosiloxanyl derivatives with ethyl hydroxyalkyl ether attached via carbon to silicon and their preparation and their use as paint raw materials and their use as intermediates for the preparation of silicone polyethers, silicone polyesters, silicone polyurethanes, silicone acrylates and silicone isocyanates. The compounds are of the general formula:

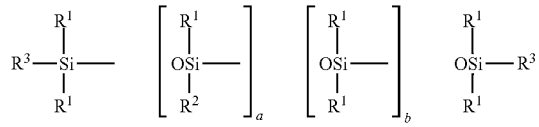

in which $R^1$=identical or different aliphatic or aromatic hydrocarbon groups, $R^2=CH_2CH_2O(CR^4R^5)_xOH$, where $R^3=R^2$ or $R^1$, a=1 to 50 and b=0 to 500.

In U.S. Pat. No. 5,939,491 is disclosed curable compositions comprising an organic polysiloxane which can contain a variety of reactive functional groups and a curing agent which contains functional groups reactive with the functional groups of the polysiloxanes. Such curable compositions are particularly useful in coating compositions which are curable at both ambient and thermal cure conditions where they provide such excellent properties as increased pot-life, improved tack-time, adhesion, mar resistance and acid etch resistance.

The curable composition comprises an organic polysiloxane containing reactive functional groups, said polysiloxane having the general structure:

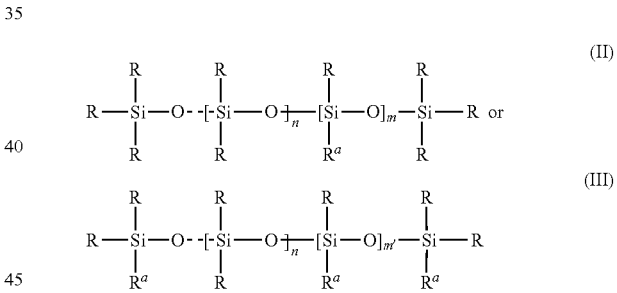

where m is at least 1; m' is 0 to 50; n is 0 to 50; R is selected from the group consisting of OH and monovalent hydrocarbon groups connected to the silicon atoms; $R^a$ has the following structure: $R_1$—O—X wherein $R_1$ is alkylene, oxyalkylene or alkylene aryl; and X is a moiety containing a functional group selected from the group consisting of OH, COOH, NCO, carboxylate such as ester, carbonate and anhydride, primary amine, secondary amine, amide, carbamate and epoxy functional groups; and a component which contains functional groups reactive with the functional groups of the organic polysiloxane. Preferably, the curable composition comprises: (a) an organic polysiloxane containing reactive functional groups, the polysiloxane having the formula (II) or (III), where m, m', n, R, Ra and X are as described above; (b) a polymer or oligomer which contains reactive functional groups; and (c) a curing agent containing functional groups which are reactive with the functional groups of (a) and (b). In one preferred embodiment n+m and n+m' is 2 or 3.

In U.S. Pat. No. 6,593,417 is disclosed a composition formed from components comprising: (a) a polysiloxane comprising at least one reactive functional group, the polysiloxane comprising at least one of the following structural units (I)

$$R^1{}_nR^2{}_mSiO_{(4-n-m)/2}$$

wherein each $R^1$, which may be identical or different, represents H, OH, or a monovalent hydrocarbon group; each $R^2$, which may be identical or different, represents a group comprising at least one reactive functional group, provided that when the polysiloxane is a partial condensate of a silanol, then less than 70% by weight of the partial condensate is the partial condensate of $CH_3Si(OH)_3$ ; and (b) a plurality of particles having an average particle size of less than 100 nanometers prior to incorporation into the composition, wherein each component is different, and herein the at least one reactive functional group of the at least one polysiloxane is substantially nonreactive with the particles.

U.S. Pat. No. 6,610,777 discloses a coating composition formed from components comprising: (a) at least one polysiloxane comprising at least one reactive functional group, the at least one polysiloxane comprising at least one of the following structural units (I):

$$R^1{}_nR^2{}_mSiO_{(4-n-m)/2} \quad (I)$$

wherein each $R^1$, which may be identical or different, represents H, OH, a monovalent hydrocarbon group or a monovalent siloxane group; each $R^2$, which may be identical or different, represents a group comprising at least one reactive functional group, wherein m and n fulfill the requirements of 0<n<4, 0<m<4 and 2<(m+n)≦4; (b) at least one polyol having a hydroxyl value ranging from 100 to 200; and (c) at least one reactant comprising at least one functional group that is reactive with at least one functional group selected from the at least one reactive functional group of the at least one polysiloxane (a) and at least one functional group of the at least one polyol (b), wherein each component is different, and wherein a coating formed from the coating composition when cured has a flexibility rating of at least 6 according to a Flexibility Test Method at a temperature of 70° F.

U.S. Pat. No.5,916,992 discloses novel polysiloxane polyols and a method for the preparation of such polysiloxane polyols. The polysiloxane polyol has the general formula:

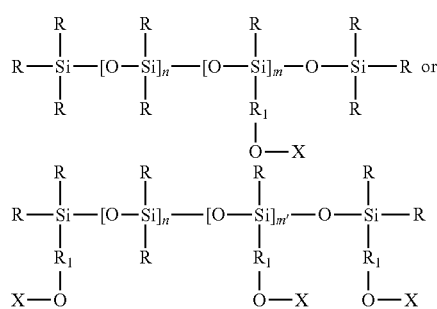

where n is 0 to 50; m is at least one; m' is 0 to 50; R is selected from the group consisting of OH and monovalent hydrocarbon groups attached to the silicon atoms; $R_1$ is alkylene, oxyalkylene or alkylene aryl; and the moiety X is H, monohydroxy-substituted alkylene or oxyalkylene, or $R_2$—$(CH_2$—$OH)_p$ wherein p is 2 or 3, and $R_2$ is

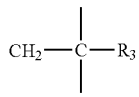

when p is 2 and $R_3$ is $C_1$ to $C_4$ alkyl, or $R_2$ is

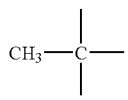

when p is 3, and wherein at least a portion of the moiety X is $R_2$—$(CH_2$—$OH)_p$.

This invention relates to a carbinol-functional silicone resin comprising the units:

$(R^1{}_3SiO_{1/2})_a$     (i)

$(R^2{}_2SiO_{2/2})_b$     (ii)

$(R^3SiO_{3/2})_c$     (iii) and $(SiO_{4/2})_d$     (iv)

wherein $R^1$ and $R^2$ are each independently a hydrogen atom, an alkyl group having from 1 to 8 carbon atoms, an aryl group, a carbinol group free of aryl groups having at least 3 carbon atoms, or an aryl-containing carbinol group having at least 6 carbon atoms, $R^3$ is an alkyl group having from 1 to 8 carbon atoms or an aryl group, a has a value of less than or equal to 0.6, b has a value of zero or greater than zero, c has a value of greater than zero, d has a value of less than 0.5, and the value of a+b+c+d=1.with the proviso that when each $R^2$ is methyl the value of b is less than 0.3 and with the proviso there is on average at least one carbinol group per resin molecule.

Another embodiment of this invention relates to a carbinol-functional silicone resin comprising the units:

$(R^1{}_3SiO_{1/2})_a$     (i)

$(R^2{}_2SiO^{2/2})_b$     (ii)

$(R_3SiO_{3/2})_c$     (iii) and $(SiO_{4/2})_d$     (iv)

wherein $R^1$ is independently a hydrogen atom, an alkyl group having from 1 to 8 carbon atoms, an aryl group, a carbinol group free of aryl groups having at least 6 carbon atoms, or an aryl-containing carbinol group having at least 6 carbon atoms, $R^2$ is a hydrogen atom, an alkyl group having from 1 to 8 carbon atoms, an aryl group, a carbinol group free of aryl groups having at least 3 carbon atoms, or an aryl-containing carbinol group having at least 6 carbon atoms, $R^3$ is an alkyl group having from 1 to 8 carbon atoms or an aryl group, a has a value of less than or equal to 0.6, b has a value of zero or greater than zero, c has a value of greater than zero, d has a value of less than 0.5, and the value of a+b+c+d=1, and with the proviso that when each $R^2$ is methyl the value of b is less than 0.3 and with the proviso that greater than 25 wt % of the $R^1$+$R^2$+$R^3$ groups in the carbinol-functional silicone resin are phenyl.

For the purposes of this invention "carbinol group" is defined as any group containing at least one carbon-bonded hydroxyl (COH) group. Thus the carbinol groups may contain more than one COH group such as for example

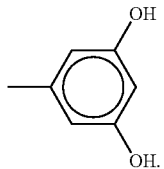

The alkyl groups of $R^1$ and $R^2$ in the carbinol functional silicone resin of Component (B) are illustrated by methyl, ethyl, propyl, butyl, pentyl, hexyl, and octyl, with the alkyl group typically being methyl. The aryl groups of $R^1$ and $R^2$ are illustrated by phenyl, naphthyl, benzyl, tolyl, xylyl, xenyl, methylphenyl, 2-phenylethyl, 2-phenyl-2-methylethyl, chlorophenyl, bromophenyl and fluorophenyl with the aryl group typically being phenyl.

The carbinol group free of aryl groups having at least 3 carbon atoms is illustrated by groups having the formula $R^4OH$ wherein $R^4$ is a divalent hydrocarbon group having at least 3 carbon atoms or a divalent hydrocarbonoxy group having at least 3 carbon atoms. The group $R^4$ is illustrated by alkylene groups selected from —$(CH_2)_x$— where x has a value of 3 to 10, —$CH_2CH(CH_3)$—, —$CH_2CH(CH_3)CH_2$—, —$CH_2CH_2CH(CH_2CH_3)CH_2CH_2CH_2$—, and —$OCH(CH_3)(CH_2)_x$— wherein x has a value of 1 to 10. The carbinol group free of aryl groups having at least 3 carbon atoms is also illustrated by groups having the formula having the formula $R^6(OH)CH_2OH$ and $R^6$ is a group having the formula —$CH_2CH_2(CH_2)_xOCH_2CH$— wherein x has a vale of 1 to 10.

The aryl-containing carbinol group having at least 6 carbon atoms is illustrated by groups having the formula $R^5OH$ wherein $R^5$ is an arylene group selected from —$(CH_2)_xC_6H_4$— wherein x has a value of 0 to 10, —$CH_2CH(CH_3)(CH_2)_xC_6H_4$—wherein x has a value of 0 to 10, and —$(CH_2)_xC_6H_4(CH_2)_x$— wherein x has a value of 1 to 10. The aryl-containing carbinol groups typically have from 6 to 14 atoms.

In the carbinol-functional silicone resin, a has a typical value of 0.1 to 0.6, alternatively 0.2 to 0.4, b has a typical value of 0 to 0.4, alternatively 0 to 0.1, c has a typical value of 0.3 to 0.8, alternatively 0.4 to 0.8, d has a typical value of 0 to 0.3, alternatively zero. When each $R^2$ is methyl the value of b is less than 0.3, alternatively less than 0.1.

The carbinol functional silicone resins have on average at least one carbinol group per resin molecule. Typically, the equivalent weight of carbinol groups on the carbinol functional silicone resin is from 100 to 1000, alternatively 200 to 800.

Typically, when $R^1$ or $R^2$ of the carbinol-functional silicone resin contains a carbinol group, only one carbinol group will be present on each such $R^1$ or $R^2$.

The carbinol-functional silicone resins are illustrated by carbinol-functional silicone resins comprising the units:

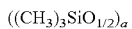

 where $R^2$=—$(CH_2)_3C_6H_4OH$

 and

, carbinol-functional silicone resins comprising the units:

$((R^1)(CH_3)_2SiO_{1/2})_a$ where $R^1$=—$(CH_2)_3C_6H_4OH$
and $(C_6H_5SiO_{3/2})_c$, carbinol-functional silicone resins comprising the units:

$((R^1)(CH_3)_2SiO_{1/2})_a$ where $R^1$=—$(CH_2)_3C_6H_4OH$
and $(CH_3SiO_{3/2})_c$, carbinol-functional silicone resins comprising the units:

$(R^1)(CH_3)_2SiO_{1/2})_a$ where $R^1$=—$(CH_2)_3OH$ and $(C_6H_5SiO_{3/2})_c$, carbinol-functional silicone resins comprising the units:

$((R^1)(CH_3)_2SiO_{1/2})_a$ where $R^1$=—$(CH_2)_3OH$ $(CH_3SiO_{3/2})_c$ and $(C_6H_5SiO_{3/2})_c$, carbinol-functional silicone resins comprising the units:

$((CH_3)_3SiO_{1/2})_a$ $((R^2)CH_3SiO_{2/2})_b$ where $R^2$=—$(CH_2)_3OH$ $((C_6H_5)CH_3SiO_{2/2})_b$ and $(C_6H_5SiO_{3/2})_c$, carbinol-functional silicone resins comprising the units:

$((CH_3)_3SiO_{1/2})_a$ $((R_1)(CH_3)_2SiO_{1/2})_a$ where $R^1$=—$(CH_2)_3OH$ and $(C_6H_5SiO_{3/2})_c$, carbinol-functional silicone resins comprising the units:

$((R^1)(CH_3)_2SiO_{1/2})_a$ where $R^1$=—$CH_2CH(CH_3)CH_2OH$ $((H)(CH_3)_2SiO_{1/2})_a$ and $(C_6H_5SiO_{3/2})_c$, and carbinol-functional silicone resins comprising the units:

$((R^1)(CH_3)_2SiO_{1/2})_a$ where $R^1$=—$(CH_2)_3OH$ $(CH_3SiO_{3/2})_c$ wherein a has a typical value of 0.1 to 0.6, b has a typical value of zero to 0.4, and c has a typical value of 0.3 to 0.8.

The carbinol-functional silicone resins can be used to make tough, water, solvent and heat resistant materials by formulating and reacting these silicone resins with certain organic materials. If desired, the $R^1+R^2+R^3$ groups in the carbinol functional silicone resin can contain high enough phenyl content to provide appropriate compatibility with other components. Typically greater than 10 weight percent of the $R^1+R^2+R^3$ groups are phenyl and even more typically greater than 25 weight percent of the $R^1+R^2+R^3$ groups are phenyl.

This invention further relates to a method of preparing carbinol-functional silicone resins comprising reacting:

(A') at least one hydrogen-functional silicone resin comprising the units:

$(R^7_3SiO_{1/2})_a$ (i)

$(R^8_2SiO_{2/2})_b$ (ii)

$(R^3SiO_{3/2})_c$ (iii) and $(SiO_{4/2})_d$ (iv)

wherein $R^7$ and $R^8$ are each independently an alkyl group having from 1 to 8 carbon atoms, an aryl group, or a hydrogen atom, $R^3$, a, b, c, and d are as defined above, the value of a+b+c+d=1, with the proviso that when each $R^8$ is methyl the value of b is less than 0.3, with the proviso that there are at least two silicon-bonded hydrogen atoms present in the silicone resin; and (B') at least one vinyl-terminated alcohol; in the presence of (C') a hydrosilylation catalyst; and optionally (D') at least one solvent.

Another embodiment of this invention relates to a method of preparing carbinol-functional silicone resins comprising reacting:

(A') at least one hydrogen-functional silicone resin comprising the units:

$(R^7_3SiO_{1/2})_a$ (i)

$(R^8_2SiO_{2/2})_b$ (ii)

$(R^3SiO_{3/2})_c$ (iii) and $(SiO_{4/2})_d$ (iv)

wherein $R^7$ and $R^8$ are each independently an alkyl group having from 1 to 8 carbon atoms, an aryl group, or a hydrogen atom, $R^3$, a, b, c, and d are as defined above, the value of a+b+c+d=1, with the proviso that when each $R^8$ is methyl the value of b is less than 0.3, with the proviso that there are at least two silicon-bonded hydrogen atoms present in the silicone resin and with the proviso that greater than 30 wt % of the $R^1+R^2+R^3$ groups phenyl; and (B') at least one vinyl-terminated alcohol; in the presence of (C') a hydrosilylation catalyst; and optionally (D') at least one solvent.

The alkyl groups and aryl groups are as illustrated above. Typically, the alkyl group is methyl and the aryl group is phenyl. In Component (A') a has a typical value of 0.1 to 0.6, alternatively 0.2 to 0.4, b has a typical value of 0 to 0.4, alternatively 0 to 0.1, c has a typical value of 0.3 to 0.8, alternatively 0.4 to 0.8, d has a typical value of 0 to 0.3, alternatively zero. When each $R^2$ is methyl the value of b is less than 0.3, alternatively less than 0.1. Typically, less than 70 weight percent of the $R^3$ groups are methyl.

"Reacting" as used herein means mixing components (A')-(C') and any optional components at room temperature (20-25° C.) or heating a mixture comprising components (A')-(C') to temperatures above room temperature such as at temperatures of up to 200° C., however it is preferred that if components (A')-(C') and any optional components are heated, they are heated to a temperature of from 70° C. to 110° C.

The hydrogen-functional silicone resins of (A') are illustrated by hydrogen-functional silicone resins comprising the units:

$((CH_3)_3SiO_{1/2})_a$ $((H)CH_3SiO_{2/2})_b$ $((C_6H_5)CH_3SiO_{2/2})_b$ and $(C_6H_5SiO_{3/2})_c$, hydrogen-functional silicone resins comprising the units:

$((H)(CH_3)_2SiO_{1/2})_a$ $(C_6H_5SiO_{3/2})_c$, hydrogen-functional silicone resins comprising the units:

$((H)(CH_3)_2SiO_{1/2})_a$ $(CH_3SiO_{3/2})_c$, hydrogen-functional silicone resins comprising the units:

$((H)(CH_3)_2SiO_{1/2})_a$ $(CH_3SiO_{3/2})_c$ and $(C_6H_5SiO_{3/2})_c$, and hydrogen-functional silicone resins comprising the units:

$((CH_3)_3SiO_{1/2})_a$ $((H)(CH_3)_2SiO_{1/2})_a$ $(C_6H_5SiO_{3/2})_c$, wherein a has a typical value in the resin of 0.1 to 0.6, b has a typical value in the resin of zero to 0.4, and c has a typical value in the resin of 0.3 to 0.8.

The amount of hydrogen-functional silicone resin Component (A') is typically from 25 to 95 weight percent, said weight percent being based on the total weight of Components (A')+(B')+(C')+(D').

Component (B'), the terminally unsaturated alcohol, is illustrated by vinyl-terminated alcohols having the formula $CH_2=CH(CH_2)_xOH$ wherein x has a value of 1 to 10, allyl-terminated alcohols having the formula $CH_2=CHCH(CH_3)(CH_2)_xOH$ wherein x has a value of 1 to 10, methylallyl-terminated alcohols having the formula $CH_2=C(CH_3)(CH_2)_xOH$ wherein x has a value of 1 to 10, vinyl-terminated alcohols having the formula $CH_2=CH(CH_2)_xC_6H_4OH$, wherein x has a value of 1 to 10, allyl-terminated alcohols having the formula $CH_2=CHCH(CH_3)(CH_2)_xC_6H_4OH$, wherein x has a value of 1 to 10, and methylallyl-terminated alcohols having the formula $CH_2=C(CH_3)(CH_2)_xC_6H_4OH$, wherein x has a value of 1 to 10. Some typical terminally unsaturated alcohols from the above include $CH_2=CHCH_2OH$, $CH_2=CHCH_2C_6H_4OH$, $CH_2=C(CH_3)CH_2OH$, and $CH_2=CHCH(CH_3)(CH_2)OH$.

The amount of terminally unsaturated alcohol, Component (B') can be from 5 to 60 weight percent, but is typically from 5 to 40 weight percent, said weight percent being based on the total weight of Components (A')+(B')+(C')+(D').

Component (C'), the hydrosilylation catalyst is illustrated by any metal-containing catalyst which facilitates the reaction of silicon-bonded hydrogen atoms of component (A') with the vinyl groups of component (B). The metals are illustrated by ruthenium, rhodium, palladium, osmium, iridium, or platinum.

The metal-containing catalyst is typically a platinum-containing catalyst since they are the most widely used and available and because they provide a more favorable effect for the compositions of this invention in terms of improved reaction rates. Platinum-containing catalysts can be a compound or complex of a platinum metal.

One type of typical platinum-containing catalyst in the compositions of this invention is the composition that is obtained when chloroplatinic acid is reacted with an aliphatically unsaturated organosilicon compound such as divinyltetramethyldisiloxane, because of its easy dispersibility in organosilicon systems.

Preferably component (C') is selected from chloroplatinic acid, alcohol modified chloroplatinic acids, olefin complexes of chloroplatinic acid, complexes of chloroplatinic acid and divinyltetramethyldisiloxane, fine platinum particles adsorbed on carbon carriers, platinum supported on metal oxide carriers such as Pt($Al_2O_3$), platinum black, platinum acetylacetonate, platinum(divinyltetramethyldisiloxane), platinous halides exemplified by $PtCl_2$, $PtCl_4$, $Pt(CN)_2$, complexes of platinous halides with unsaturated compounds exemplified by ethylene, propylene, and organovinylsiloxanes, styrene hexamethyldiplatinum, and $RhCl_3(Bu_2S)_3$.

The amount of hydrosilylation catalyst that is used is not narrowly limited as long as there is a sufficient amount to accelerate a reaction between Components (A') and (B') at room temperature or at temperatures above room temperature. The exact necessary amount of this catalyst will depend on the particular catalyst utilized and is not easily predictable. However, for platinum-containing catalysts the amount can be as low as one weight part of platinum for every one million weight parts of components (A')+(B'). The catalyst can be added at an amount 10 to 120 weight parts per one million parts of components (A')+(B'), but is typically added in an amount from 10 to 60 weight parts per one million parts of components (A')+(B').

Component (D') the solvent can be an alcohol such as methanol, ethanol, isopropanol, butanol, or n-propanol, a ketone such as acetone, methylethyl ketone, or methyl isobutyl ketone; an aromatic hydrocarbon such as benzene, toluene, or xylene; an aliphatic hydrocarbon such as heptane, hexane, or octane; a glycol ether such as propylene glycol methyl ether, dipropylene glycol methyl ether, propylene glycol n-butyl ether, propylene glycol n-propyl ether, or ethylene glycol n-butyl ether, a halogenated hydrocarbon such as dichloromethane, 1,1,1-trichloroethane or methylene chloride, chloroform, dimethyl sulfoxide, dimethyl formamide, acetonitrile, tetrahydrofuran, white spirits, mineral spirits, or naphtha.

The amount of solvent, Component (D'), can be up to 50 weight percent, but is typically from 20 to 50 weight percent, said weight percent being used on the total weight of Components (A')+(B')+(C')+(D').

This invention also relates to an emulsion composition comprising: (A) a carbinol-functional silicone resin comprising the units:

$$(R^1_3SiO_{1/2})_a \quad (i)$$

$$(R^2_2SiO_{2/2})_b \quad (ii)$$

$$(R^3SiO_{3/2})_c \quad (iii) \text{ and}$$

$$(SiO_{4/2})_d \quad (iv)$$

wherein $R^1$ and $R^2$ are each independently a hydrogen atom, an alkyl group having from 1 to 8 carbon atoms, an aryl group, a carbinol group free of aryl groups having at least 3 carbon atoms, or an aryl-containing carbinol group having at least 6 carbon atoms, $R^3$ is an alkyl group having from 1 to 8 carbon atoms or an aryl group, a has a value of zero or greater than zero or equal to 0.6, b has a value of zero or greater than zero, c has a value of greater than zero, d has a value of less than 0.5, and the value of a+b+c+d=1, and with the proviso that when each $R^2$ is methyl the value of b is less than 0.3, and with the proviso there is on average at least one carbinol group per resin molecule; (B) at least one surfactant; and (C) water.

The carbinol-functional silicone resin of Component (A) is as described above including typical embodiments thereof. The amount of Component (A) in the emulsion composition is typically from 25 to 75 weight percent, said weight percent being based on the total weight of the emulsion composition.

Component (B) is at least one surfactant. The surfactant may be an anionic, cationic, nonionic, or amphoteric surfactant. The surfactants may be employed separately or in combinations of two or more. Examples of suitable anionic surfactants include alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid.

Examples of cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylammonium hydroxide, or hexadecyltrimethylammonium hydroxide, dialkyldimethylammonium hydroxides such as octyldimethylammonium hydroxide, decyldimethylammonium hydroxide, didodecyldimethyiammonium hydroxide, dioctadecyidimethylammonium hydroxide, tallow trimethylammonium hydroxide, coconut oil, trimethylammonium hydroxide, methylpolyoxyethylene cocoammonium chloride, and dipalmityl hydroxyethylammonium methosulfate, amide derivatives of amino alcohols such as beta-hydroxylethylstearylamide, and amine salts of long chain fatty acids.

Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

Examples of the amphoteric surfactants that can be used include amino acid surfactants and betaine acid surfactants.

Typical commercially available surfactants include trimethylnonyl polyethylene glycol ethers and polyethylene glycol ether alcohols containing linear alkyl groups having from 11 to 15 such as 2,6,8-trimethyl-4-nonyloxypolyethylene oxyethanol (6 EO) (sold as Tergitol®TMN-6 by The Dow Chemical Company, Midland, Mich.), 2,6,8-trimethyl-4-nonyloxypolyethylene oxyethanol (10 EO) (sold as Tergitol®TMN-10 by The Dow Chemical Company, Midland, Mich.), alkylene-oxypolyethylene oxyethanol ($C_{11-15}$ secondary alkyl, 9 EO) (sold as Tergitol®15-S-9 by The Dow Chemical Company, Midland, Mich.), alkylene-oxypolyethylene oxyethanol ($C_{11-15}$ secondary alkyl, 15 EO) (sold as Tergito®15-S-15 by The Dow Chemical Company, Midland, Mich.), octylphenoxy polyethoxy ethanols having varying amounts of ethylene oxide units such as octylphenoxy polyethoxy ethanol (40 EO) (sold as Triton® X405 by Rohm and Haas Company, Philadelphia, Pa.), nonionic ethoxylated tridecyl ethers available from Emery Industries, Mauldin, S.C. under the general tradename Trycol, alkali metal salts of dialkyl sulfosuccinates available from American Cyanamid Company, Wayne, N.J. under the general tradename Aerosol, polyethoxylated quaternary ammonium salts and ethylene oxide condensation products of the primary fatty amines, available from Armak Company, Chicago, Ill. under the tradenames Ethoquad, Ethomeen, or Arquad, and polyoxyalkylene glycol modified polysiloxanes. These preferred surfactants may also be obtained from other suppliers under different tradenames.

Surfactants useful in the invention also include those derived from silicone, sorbitan derivatives, and fatty alcohol derivatives. More specifically, suitable surfactants include, but are not limited to, sorbitan sesquioleate, sorbitan oleate, sorbitan isostearate; alkoxylated alcohols such as ethoxylated fatty alcohols including laureth-4, laureth-7, deceth-12, steareth-10; hydroxylated derivatives of polymeric silicones, such as dimethicone copolyol; alkylated derivatives of hydroxylated polymeric silicones such as cetyl dimethicone copolyol; glyceryl esters such as polyglyceryl-4-isostearate; and mixtures thereof, especially mixtures of hydroxylated derivatives of polymeric silicones, alkylated derivatives of hydroxylated polymeric silicones and glyceryl esters, most especially mixtures of dimethicone copolyol, cetyl dimethicone copolyol and polyglyceryl-4-isostearate. Most preferred is a mixture of such surfactants, i.e. a dimethicone copolyol, sorbitan sesquioleate and laureth-7.

The amount of Component (B) in the emulsion composition is typically from 1 to 20 weight percent, said weight percent being based on the total weight of the emulsion composition.

Component (C) is water. Typically, water is present at a level of from about 20 to 80 weight percent, said weight percent being based on the total weight of the emulsion composition.

The emulsion compositions of this invention can further comprise fragrances, preservatives, vitamins, ceramides, amino-acid derivatives, liposomes, polyols, such as glycerine and propylene glycol and botanicals (plant extracts) and additional conditioning agents such as quaternary polymers or silicone materials. Other additives can include, but are not limited to the following. depending on the use, glycols, vitamins A, vitamin C and vitamin E in their various forms, Pro-Vitamin B5, sunscreen agents (these include those which absorb ultraviolet light between about 290-320 nanometers (the LW-B region) and those which absorb ultraviolet light in the range of 320-400 (the LW-B region)), humectants, preservatives, such as known parabens, emollients, occlusive agents, and esters. Other additives can include pigments especially when the emulsion is used as a make-up.

The compositions according to the invention can also contain agents for artificially tanning and/or browning the skin (self-tanning agents), such as, for example, dihydroxyacetone (DHA). These optional ingredients can be present in the emulsion compositions of this invention up in an amount of up to 5 parts by weight per 100 parts by weight of emulsion composition, but typically are present in amount of from 0.1 to 1 part by weight per 100 parts by weight of emulsion composition. Also the emulsion can be spray dried to form a resin/active composite particle.

The emulsion compositions of this invention may be prepared by mixing (or mechanically agitating) components (A)-(C), and any optional components, to form a homogenous mixture. This may be accomplished by any convenient mixing method known in the art exemplified by a spatula, mechanical stirrers, in-line mixing systems containing baffles and/or blades, powered in-line mixers, homogenizers, a drum roller, a three-roll mill, a sigma blade mixer, a bread dough mixer, and a two roll mill. The order of mixing is not considered critical.

EXAMPLES

Silicone Resins A1-A8

Phenyltrimethoxysilane, methyltrimethoxysilane, and/or phenylmethyldimethoxysilane, catalyzed by trifluoromethanesulfonic acid (TFMSA) were hydrolyzed with deionized water, followed by distillative removal of by-product methanol. 1,1,3,3-tetramethyl-1,3-disiloxane (TMDS) and/or methylhydrogencyclosiloxanes and acetic acid were added and the mixture heated to 50° C. for three hours. (Optionally hexamethyldisiloxane (HMDS) and additional acetic acid were also added.) Methanol and methyl acetate were removed via distillation, followed optionally by adding more acetic acid and additional heating at 50° C. Hydrocarbon solvent was added and the mixture washed with saturated aqueous sodium bicarbonate and multiple aliquots of deionized water, filtered if needed and solvent optionally removed. The amounts of the ingredients are listed in Table 1 below. The resulting product is shown in Table 2 below.

Silicone Resin B1

6240 grams (g) of phenyltrimethoxysilane was dissolved in 1875.36 g of dimethoxyethane and this was hydrolyzed with 1291.68 g of a 1 wt % aqueous solution of HCl at reflux for one hour, followed by distillative removal of by-product methanol and some solvent. An additional 1872 g of solvent and 131.04 g of a 1 wt % aqueous HCl were added and additional volatiles removed by distillation. An additional 2126.4 g of dimethoxyethane was added, then the structure sequentially capped with 1181.62 g of chlorodimethylsilane and 80.71 g of chlorotrirethylsilane. Volatiles were removed via distillation and the product dissolved in 3725.8 g of toluene and washed with aliquots of saturated aqueous sodium bicarbonate and water. 406 g of water and 2035 g of dimethoxyethane were added and removed via distillation. This step was repeated using 1218 g of water and 2500 ml of dimethoxyethane, followed by distillative removal of all volatiles to yield 4100 g of product. The composition of silicone resin B1 was determined by NMR analysis to be $M^H 0.20 T^{Ph} 0.80$.

Silicone Resin C1

4958.4 g of methyltrimethoxysilane was hydrolyzed with 252.3 g of deionized water in the presence of 4.93 g of trifluoromethanesulfonic acid. 5456.4 g of 1,1,3,3-tetramethyl-1,3-disiloxane (TMDS) and an additional 725.8 g of deionized water were added. Volatiles were removed via distillation, then the product mixture dissolved in 2210 g of hexane. The product solution was washed with saturated aqueous sodium bicarbonate and multiple aliquots of deionized water, dried over magnesium sulfate, filtered and solvent removed. The composition of silicone resin C1 was determined by NMR analysis to be $M^H{}_{0.55}T^{Me}{}_{0.45}$.

Examples 1-12

A catalytic amount of 1% Pt(Al$_2$O$_3$) was added, followed by addition of either allyl alcohol or allyl phenol. The mixture was heated at 70-110° C. until the SiH was consumed, as determined by following the disappearance of its peak in the FTIR spectrum (~2165 cm$^{-1}$). Optionally, triphenylphosphine and carbon black were added. The product mixture was filtered and solvent removed. The silicone resin type, reagent weights, yield, and resin composition are shown in Table 3 below.

TABLE 1

| Silicone Resin | PhSi(OMe)$_3$ | MeSi(OMe)$_3$ | PhMeSi(OMe)$_2$ | TFMSA | TMDS | MeH Cyclics | HMDS | Heptane | Water | Acetic Acid | Yield (g) |
|---|---|---|---|---|---|---|---|---|---|---|---|
| A1 | 4752.0 | | | 2.1 | 1316.3 | | | 1299.8 | 501.0 | 588.6 | 4051.6 |
| A2 | 793.4 | | 364.6 | 0.6 | | 120.3 | 162.7 | 459.0 | 90.2 | 212.7 | 1040.8 |
| A3 | 2379.5 | 1634.6 | | 2.3 | 1316.4 | | | 1800.0 | 500.9 | 588.6 | 3385.0 |
| A4 | 3668.4 | | | 1.9 | 3668.7 | | | 1387.5 | 190.5 | 1640.1 | 4578.9 |
| A5 | 1546.6 | | | 0.7 | 88.7 | | 267.9 | 527.3 | 169.2 | 277.4 | 1361.0 |
| A6 | 4752.0 | | | 2.2 | 1316.4 | | | 1800.0 | 500.9 | 588.6 | 4050.3 |
| A7 | 119.0 | 165.5 | | 0.2 | 88.7 | | | 246.8 (toluene) | 37.9 | 39.6 | 480.2 (soln) |
| A8 | 204.4 | 204 | | 0.19 | 88.7 | | | 228.1 (toluene) | 37.9 | 39.6 | 431.6 (soln) |

TABLE 2

| Silicone Resin | Hydrogen-functional Silicone Resin |
|---|---|
| A1 | $M^H{}_{0.41}T^{Ph}{}_{0.59}$ |
| A2 | $M_{0.195}D^H{}_{0.202}D^{Ph}{}_{0.202}T^{Ph}{}_{0.303}$ |
| A3 | $M^H{}_{0.393}T^{Me}{}_{0.304}T^{Ph}{}_{0.303}$ |
| A4 | $M^H{}_{0.634}T^{Ph}{}_{0.366}$ |
| A5 | $M_{0.266}M^H{}_{0.098}T^{Ph}{}_{0.637}$ |
| A6 | $M^H{}_{0.40}T^{Ph}{}_{0.60}$ |
| A7* | $M^H{}_{0.4}T^{Me}{}_{0.4}T^{Ph}{}_{0.2}$ |
| A8* | $M^H{}_{0.4}T^{Me}{}_{0.5}T^{Ph}{}_{0.1}$ |

*approximate compositions

In Table 2 above:
M denotes (CH$_3$)$_3$SiO$_{1/2}$
$M^H$ denotes H(CH$_3$)$_2$SiO$_{1/2}$
$D^H$ denotes H(CH$_3$)SiO$_{2/2}$
$D^{Ph}$ denotes C$_6$H$_5$(CH$_3$)SiO$_{2/2}$
$T^{Me}$ denotes CH$_3$SiO$_{3/2}$
$T^{Ph}$ denotes C$_6$H$_5$SiO$_{3/2}$

TABLE 3

| Example | Carbinol-functional Silicone Resin Composition (CSR) | Silicone Resin Type | Silicone Resin Amount | Allyl alcohol* | Allyl phenol | Xylenes | 1% Pt/Al$_2$O$_3$ | Yield (g) |
|---|---|---|---|---|---|---|---|---|
| Ex1 | $M_{0.193}D^{phenol}{}_{0.156}D^{Ph}{}_{0.228}T^{Ph}{}_{0.395}$ | A2 | 250.1 | | 65.2 | 167.0 | 1.2 | 303.7 |
| Ex2 | $M^{Phenol}{}_{0.387}T^{Ph}{}_{0.586}$ | A1 | 250.2 | | 140.6 | 107.8 | 1.3 | 375.9 |
| Ex3 | $M^{Phenol}{}_{0.196}T^{Ph}{}_{0.780}$ | B1 | 250.0 | | 63.1 | 250.0 | 1.3 | N/A |
| Ex4 | $M^{PrOH}{}_{0.60}T^{Ph}{}_{0.378}$ | A4 | 253.1 | 305.6 | | 250.1 | 0.8 | 343.4 |
| Ex5 | $M^{PrOH}{}_{0.355}T^{Me}{}_{0.314}T^{Ph}{}_{0.314}$ | A3 | 249.9 | 196.5 | | 250.0 | 1.8 | 301.9 |
| Ex6 | $M^{PrOH}{}_{0.387}T^{Ph}{}_{0.583}$ | A1 | 250.0 | 166.0 | | 251.0 | 2.1 | 297.0 |
| Ex7 | $M_{0.196}D^{PrOH}{}_{0.172}D^{Ph}{}_{0.208}T^{Ph}{}_{0.397}$ | A2 | 227.9 | 73.6 | | 151.9 | 2.0 | 248.8 |
| Ex8 | $M^{PrOH}{}_{0.180}T^{Ph}{}_{0.793}$ | B1 | 250.1 | 74.6 | | 250.1 | 3.6 | 268.9 |
| Ex9 | $M_{0.261}M^{PrOH}{}_{0.082}T^{Ph}{}_{0.628}$ | A5 | 249.8 | 37.1 | | 251.4 | 2.5 | 268.9 |
| Ex10** | $M^{PrOH}{}_{0.372}T^{Me}{}_{0.415}T^{Ph}{}_{0.192}$ | A7 | 480.2 (soln) | 209.1 | | | 1.0 | 288.0 |

TABLE 3-continued

| Example | Carbinol-functional Silicone Resin Composition (CSR) | Silicone Resin Type | Reagent Weights (g) | | | | | Yield (g) |
|---|---|---|---|---|---|---|---|---|
| | | | Silicone Resin Amount | Allyl alcohol* | Allyl phenol^ | Xylenes | 1% Pt/Al$_2$O$_3$ | |
| Ex11 | M$^{PrOH}_{0.502}$T$^{Me}_{0.450}$ | C1 | 250.2 | 345.7 | | 250.3 | 0.8 | 348.2 |
| ex12** | M$^{PrOH}_{0.361}$T$^{Me}_{0.517}$T$^{Ph}_{0.101}$ | A8 | 431.6 (soln) | 209.1 | | | 0.9 | 260.5 |

**Formulation included 0.04 grams of triphenylphosphine
In Table 3 above:
M$^{PrOH}$ denotes (HO(CH$_2$)$_3$)(CH$_3$)$_2$SiO$_{1/2}$
D$^{PrOH}$ denotes (HO(CH$_2$)$_3$)(CH$_3$)SiO$_{2/2}$
M$^{Phenol}$ denotes (HOC$_6$H$_4$(CH$_2$)$_3$)(CH$_3$)$_2$SiO$_{1/2}$
D$^{phenol}$ denotes (HOC$_6$H$_4$(CH$_2$)$_3$)(CH$_3$)SiO$_{2/2}$
M denotes (CH$_3$)$_3$SiO$_{1/2}$
D denotes (CH$_3$)$_2$SiO$_{2/2}$
D$^{Ph}$ denotes (C$_6$H$_5$)(CH$_3$)SiO$_{2/2}$
T$^{Ph}$ denotes C$_6$H$_5$SiO$_{3/2}$
T$^{me}$ denotes CH$_3$SiO$_{3/2}$
*allyl alcohol: denotes CH$_2$=CHCH$_2$OH
^allyl phenol: denotes CH$_2$=CHCH$_2$C$_6$H$_4$OH Example 13

One of the silicone resins prepared above were optionally dissolved in toluene and heated to 70-100° C. A catalytic amount of 0.52% platinum(divinyltetramethyldisiloxane) (platinum catalyst) was added, followed by methallyl alcohol. The mixture was heated at 70-110° C. until the SiH was consumed, as determined by following the disappearance of its peak in the FTIR spectrum (~2165 cm$^{-1}$). The product mixture was optionally filtered and solvent removed. The silicone resin type, reagent weights, yield, and resin composition are shown in Table 4 below.

TABLE 4

| Example | Carbinol-functional Silicone Resin Composition (CSR) | Silicone Resin Type | Reagent Weights (g) | | | | Yield (g) |
|---|---|---|---|---|---|---|---|
| | | | SiH Resin | Methallyl alcohol* | Platinum catalyst | | |
| 13 | M$^{iBuOH}_{0.310}$M$^{H}_{0.052}$T$^{Ph}_{0.609}$ | A6 | 50 | 67 | 0.75 | | 73.9 |

In Table 4 above:
Mi$^{BuOH}$ denotes (HOCH$_2$CH(CH$_3$)CH$_2$)(CH$_3$)$_2$SiO$_{1/2}$
M$^{H}$ denotes (H)(CH$_3$)$_2$SiO$_{1/2}$
T$^{Ph}$ denotes C$_6$H$_5$SiO$_{3/2}$
*methallyl alcohol denotes CH$_2$=C(CH$_3$)CH$_2$OH Examples 14 and 15

ORGANOSILICASOL™ IPA-ST—a 10-15 nm colloidal silica dispersion 30% solids in isopropyl alcohol, available from Nissan Chemicals Ind. Ltd, Japan.
DOW CORNING® Z-6124 Silane—phenyltrimethoxysilane, available from Dow Corning Corp., Midland Mich.
DOW CORNING® 3-7010 Fluid—tetramethyldisiloxane, available from Dow Corning Corp., Midland Mich.
FC-24—trifluoromethanesulfonic acid, available from 3M, St. Paul, Minn.
Triphenylphosphine—available from Sigma-Aldrich Chemical Co. Milwaukee Wis.
DARCO® G-60 activated carbon from Norit Americas, Inc. Corporation Amersfoort The Kingdom of Netherlands Georgia.
Allyl alcohol (Sigma-Aldrich Chemical Co. Milwaukee Wis.)
Tetraethoxysilane (Sigma-Aldrich Chemical Co. Milwaukee Wis.)

Example 14

A mixture of 225.0 g of phenyltrimethoxysilane and 111.5 g of ORGANOSILICASOL™ IPA-ST was hydrolyzed with 42.9 g of water and 0.12 g of concentrated HCl. After heating to reflux for 15 minutes, 256.8 g of toluene, 76.2 g of tetramethyldisiloxane and 0.36 g of trifluoromethanesulfonic acid were added and the mixture heated at 65° C. for three hours. Volatiles were removed via distillation and 2.4 g of calcium carbonate added. The mixture was filtered and additional solvent removed via distillation. 1.38 g of 1 wt % Pt/Al$_2$O$_3$ (catalyst) and 197.8 g of allyl alcohol were added and the mixture heated to reflux for 2.5 hours. 0.06 g of triphenylphosphine and 1 g of DARCO® G60 were added. The mixture was filtered and solvent removed via distillation under vacuum to yield 293.2 g of an opalescent colorless liquid. The resin was analyzed by Si$^{29}$ NMR and found to have the following composition: M$^{PrOH}_{0.38}$T$^{Ph}_{0.41}$Q$_{0.21}$.

Example 15

A 2-L flask was charged with 93.8 g of tetraethoxysilane, 356.9 g of phenyltrimethoxysilane, 108.1 g of dimethyldimethoxysilane, 0.3 g of trifluoromethanesulfonic acid premixed in 2.1 g of water. The mixture was heated to 50° C. for one hour, then further hydrolyzed with 91.6 g of additional water. 200 g of toluene, 93.8 g of tetramethyldisiloxane and 148.0 g of acetic acid were added and heating continued at 50° C. for two hours. After volatiles were removed via distillation, the mixture was washed with sodium bicarbonate solution and water, then dried via azeotropic distillation to yield a clear solution with 43% non-volatile content. About 767.6 g of this solution was heated to 95° C. followed by addition of 1.84 g of 1% Pt/Al$_2$O$_3$ and 154.4 g of allyl alcohol, then heated at reflux for fifteen hours. Next about 0.074 g of triphenylphosphine and about 1 g of carbon black were added. The mixture was filtered and volatiles removed via distillation, followed by dissolution in 125 g of butyl acetate to yield a slightly hazy colorless product solution (75% solids). Si$^{29}$ NMR analysis of the product revealed the following composition M$^{PrOH}_{0.26}$D$_{0.21}$T$^{Ph}_{0.41}$Q$_{0.10}$ where M$^{PrOH}$, D, T$^{Ph}$, and Q are as defined above.

Examples 16-23, Control, and Comparison Example 1

Polyol: Desmophen® 870 BA is a hydroxyl-functional polyacrylate resin supplied in butyl acetate (70% solids) by Bayer Corporation (Pittsburgh, Pa.).
Isocyanate: Desmodur N-3390 is a polyisocyanate based on hexamethylene diisocyanate (HDI) supplied in butyl acetate (90% solids) by Bayer Corporation (Pittsburgh, Pa.).
BA: n-butyl acetate.
Linear is 3-hydroxypropyl terminated polydimethylsiloxane.

A control coating contained only polyol, isocyanate and BA as described above.

4—Slight dewetting and/or edge crawling; minimal defects

3—Moderate dewetting and/or edge crawling; minimal defects

2—Extensive dewetting and/or edge crawling; Few defects

1—Extensive dewetting and/or edge crawling; Numerous defects

0—Severe dewetting and/or edge crawling; Extensive defects

The above isocyanate, above polyol, one of the carbinol-functional silicone resins prepared in Table 3 above (denoted CSR in Table 5), and n-butyl acetate (solvent) were added to a mixing dish and stirred vigorously with a spatula. Testing was performed on polished steel panels. The formulations were applied via 6 mil (wet) drawdown bar. The coated panels were allowed to air dry for fifteen minutes and then oven cured for 30 minutes at 265° F. The appearance of the cured films were evaluated for appearance with 1=poor and 5=excellent and the values recorded in Table 5.

The cured films were then coated perpendicular to the original coating with the identical formulation (like on like) and the second coat was cured identical to the first coat (air dry for fifteen minutes and then oven cured for 30 minutes at 265° F.). The recoatability of each formulation was evaluated and recorded in Table 5.

TABLE 5

(in (g)) Coating Formulations

| Components | Control | Ex 16 | Ex 17 | Ex 18 | Ex 19 | Ex 20 | Ex 21 | Ex 22 | Ex 23 | Cex 1 | Wt % Phenyl in CSR |
|---|---|---|---|---|---|---|---|---|---|---|---|
| Polyol | 15.5 | 11.4 | 12.5 | 12.7 | 14.2 | 13.2 | 12.2 | 12.1 | 11.1 | 13.5 | |
| BA | 3.2 | 3.2 | 3.2 | 3.2 | 3.2 | 2.7 | 3.2 | 3.2 | 3.2 | 3.2 | |
| Ex4 CSR | | 1.5 | | | | | | | | | 35.3 |
| Ex5 CSR | | | 1.6 | | | | | | | | 40 |
| Ex6 CSR | | | | 1.6 | | | | | | | 56.6 |
| Ex7 CSR | | | | | 1.7 | | | | | | 62.2 |
| Ex14 CSR | | | | | | 2.2 | | | | | 52 |
| Ex10 CSR | | | | | | | 1.6 | | | | 34 |
| Ex12 CSR | | | | | | | | 1.6 | | | 21 |
| Ex11 CSR | | | | | | | | | 1.5 | | 0 |
| Linear | | | | | | | | | | 1.7 | 0 |
| Isocyanate | 6.3 | 6.3 | 6.3 | 6.3 | 6.3 | 6.3 | 6.3 | 6.3 | 6.3 | 6.3 | |
| Total | 25 | 22 | 24 | 24 | 25 | 24 | 23 | 23 | 22 | 25 | |
| Wt % Siloxane Resin (solids) | 0 | 10 | 10 | 10 | 10 | 10 | 10 | 10 | 10 | 10 | |
| Initial Coating Quality 1 = poor 5 = perfect | 3 | 4 | 1* | 4 | 3 | 3 | 1* | 1* | 1* | 2* | |
| Recoatability (Like on Like) 1 = poor 5 = perfect | 2 | 4 | 2 | 4 | 3 | 3 | 3 | 1 | 1 | 1 | |

1* - severe orange peel
2* - uniform but hazy

RECOATABILITY: The conditions (Application method, film thickness and cure schedule) for this test are specified relative to the specific coating formulation. After the initial cure, the specimen is overcoated with the same paint formulation. After curing the second coat, the panels are rated in regards to the ability of the second coat to wet the underlying film.

5—Excellent wetting and flow; no film defects such as craters and fisheyes

All of the coating formulations listed in Table 5 cured to a dry film under the cure conditions described. The coatings prepared with carbinol functional resins produced good quality coatings that can be recoated readily if the phenyl content is sufficient to provide compatibility with the other coating components. Utilizing the same isocyanate and polyol as used in the control coating formulation over 25 wt % phenyl was required to achieve good compatibility and coating quality. The comparative coating (Cex1) prepared using the linear carbinol functional dimethylsiloxane material exhibited poor coating quality and poor recoatability.

Example 24

About 6 g of Ex4 CSR having a viscosity of 4.7 Pa·s at 22° C., was weighed into a 20 ml vial followed by 0.20 g of $C_{12-14}$ secondary alcohol ethoxylate having an HLB of 10.6 (Tergitol® 15-S-5 from The Dow Chemical Company, Midland Mich.), 0.20 g of $C_{12-14}$ secondary alcohol ethoxylate having an HLB of 18.0 (Tergitol® 15-S-40 from The Dow Chemical Company, Midland Mich.) and 3.6 g DI (deionized) water. The composition was subjected to high shear using laboratory ultrasonic processor (Fisher Model 550 Sonic Dismembrator) equipped with a microtip. The tip was placed approximately 1 cm below the surface of the liquid and the ultrasonic probe was energized to 50% of the 550 watts maximum power for 20 seconds. A milky white emulsion began to form almost instantly upon energizing the ultrasonic probe. The vial was removed from the probe, a cap placed on the vial and the vial was shaken. The vial was returned to the ultrasonic probe and the probe was energized at the same power setting for another 30-second period. The vial was again removed, capped and shaken then returned to the ultrasonic probe. This procedure was repeated such that the contents of the vial experienced 80 seconds of ultrasonic processing. The resulting composition consisted of an approximately 60% by weight, aqueous, oil/water emulsion of a carbinol-functional silicone resin having the following particle size characteristics: D(v, 0.5)=0.742 um and D(v, 0.9)=3.22 um.

The invention claimed is:

1. A carbinol-functional silicone resin comprising the units:

$(R^1_3SiO_{1/2})_a$         (i)

$(R^2_2SiO_{2/2})_b$         (ii)

$(R^3SiO_{3/2})_c$         (iii) and $(SiO_{4/2})_d$         (iv)

wherein $R^1$ and $R^2$ are each independently a hydrogen atom, an alkyl group having from 1 to 8 carbon atoms, an aryl group, or a carbinol group free of aryl groups having at least 3 carbon atoms, $R^3$ is an alkyl group having from 1 to 8 carbon atoms or an aryl group, a has a value of less than or equal to 0.6, b has a value of zero or greater than zero, c has a value of greater than zero, d has a value of less than 0.5, and the value of a+b+c+d=1, with the proviso that when each $R^2$ is methyl the value of b is less than 0.3 and with the proviso there is on average at least one carbinol group per resin molecule and greater than 10 wt % of the $R^1+R^2+R^3$ groups in the carbinol-functional silicone resin are phenyl.

2. A carbinol-functional silicone resin of claim 1 wherein
the alkyl group is methyl;
the aryl group is phenyl;
the carbinol group free of aryl groups having at least 3 carbon atoms is selected from a group having the formula $R^4OH$ wherein $R^4$ is selected from
(1) a group having the formula $-(CH_2)_x-$ where x has a value of 3 to 10,
(2) $-CH_2CH(CH_3)-$,
(3) $-CH_2CH(CH_3)CH_2-$,
(4) $-CH_2CH_2CH(CH_2CH_3)CH_2CH_2CH_2-$, and
(5) a group having the formula $-OCH(CH_3)(CH_2)_x-$ wherein x has a value of 1 to 10 and a group having the formula $R^6(OH)$ wherein $R^6$ is a group having the formula $-CH_2CH_2(CH_2)_xOCH_2CH-$ wherein x in each case has a value of 1 to 10.

3. The carbinol-functional silicone resin of claim 1 where a has a value of 0.1 to 0.6, b has a value of 0 to 0.4, c has a value of 0.3 to 0.8, and d has a value of 0 to 0.3.

4. The carbinol-functional silicone resin according to claim 1 wherein the carbinol-functional silicone resin is selected from carbinol-functional silicone resins comprising the units:

$((R^1)(CH_3)_2SiO_{1/2})_a$ where $R^1=-(CH_2)_3OH$ and $(C_6H_5SiO_{3/2})_c$, carbinol-functional silicone resins comprising the units:

$((R^1)(CH_3)_2SiO_{1/2})_a$ where $R^1=-(CH_2)_3OH$ $(CH_3SiO_{3/2})_c$ and $(C_6H_5SiO_{3/2})_c$, carbinol-functional silicone resins comprising the units:

$((CH_3)_3SiO_{1/2})_a$ $((R^2)CH_3SiO_{2/2})_b$ where $R^2=-(CH_2)_3OH$ $((C_6H_5)CH_3SiO_{2/2})_b$ and $(C_6H_5SiO_{3/2})_c$, carbinol-functional silicone resins comprising the units:

$((CH_3)_3SiO_{1/2})_a$ $((R^1)(CH_3)_2SiO_{1/2})_a$ where $R^1=-(CH_2)_3OH$ and $(C_6H_5SiO_{3/2})_c$, carbinol-functional silicone resins comprising the units:

$((R^1)(CH_3)_2SiO_{1/2})_a$ where $R^1=-CH_2CH(CH_3)CH_2OH$ $((H)(CH_3)_2SiO_{1/2})_a$ and $(C_6H_5SiO_{3/2})_c$, wherein a has a value of 0.1 to 0.6, b has a value of zero to 0.4, and c has a value of 0.3 to 0.8.

5. The carbinol-functional silicone resin according to claim 1, wherein greater than 25 weight percent of the $R^1+R^2+R^3$ groups are phenyl.

6. A carbinol-functional silicone resin comprising the units:

$(R^1_3SiO_{1/2})_a$         (i)

$(R^2_2SiO_{2/2})_b$         (ii)

$(R^3SiO_{3/2})_c$         (iii) and $(SiO_{4/2})_d$         (iv)

wherein $R^1$ is independently a hydrogen atom, an alkyl group having from 1 to 8 carbon atoms, an aryl group, or a carbinol group free of aryl groups having at least 6 carbon atoms, $R^2$ is a hydrogen atom, an alkyl group having from 1 to 8 carbon atoms, an aryl group, or a carbinol group free of aryl groups having at least 3 carbon atoms, $R^3$ is an alkyl group having from 1 to 8 carbon atoms or an aryl group, a has a value of less than or equal to 0.6, b has a value of zero or greater than zero, c has a value of greater than zero, d has a value of less than 0.5, and the value of a+b+c+d=1, and with the proviso that when each $R^2$ is methyl the value of b is less than 0.3 and with the proviso that greater than 25 wt % of the $R^1+R^2+R^3$ groups in the carbinol-functional silicone resin are phenyl.

7. The carbinol-functional silicone resin according to claim 6 wherein the carbinol-functional silicone resin is selected from
carbinol-functional silicone resins comprising the units:

$((R^1)(CH_3)_2SiO_{1/2})_a$ where $R^1$=—$(CH_2)_3OH$ and $(C_6H_5SiO_{3/2})_c$, carbinol-functional silicone resins comprising the units:

$((R^1)(CH_3)_2SiO_{1/2})_a$ where $R^1$=—$(CH_2)_3OH$ $(CH_3SiO_{3/2})_c$ and $(C_6H_5SiO_{3/2})_c$, carbinol-functional silicone resins comprising the units:

$((CH_3)_3SiO_{1/2})_a$ $((R^2)CH_3SiO_{2/2})_b$ where $R^2$=—$(CH_2)_3OH$ $((C_6H_5)CH_3SiO_{2/2})_b$ and $(C_6H_5SiO_{3/2})_c$, carbinol-functional silicone resins comprising the units:

$((CH_3)_3SiO_{1/2})_a$ $((R^1)(CH_3)_2SiO_{1/2})_a$ where $R^1$=—$(CH_2)_3OH$ and $(C_6H_5SiO_{3/2})_c$, carbinol-functional silicone resins comprising the units:

$((R^1)(CH_3)_2SiO_{1/2})_a$ where $R^1$=—$CH_2CH(CH_3)$
$\quad CH_2OH$ $((H)(CH_3)_2SiO_{1/2})_a$ and $(C_6H_5SiO_{3/2})_c$, wherein a has a value of 0.1 to 0.6, b has a value of zero to 0.4, and c has a value of 0.3 to 0.8.

8. A method of preparing carbinol-functional silicone resins comprising reacting:

(A') at least one hydrogen-functional silicone resin comprising the units:

$(R^7_3SiO_{1/2})_a$ (i)

$(R^8_2SiO_{2/2})_b$ (ii)

$(R^3SiO_{3/2})_c$ (iii) and $(SiO_{4/2})_d$ (iv)

wherein $R^7$ and $R^8$ are each independently an alkyl group having from 1 to 8 carbon atoms, an aryl group, or a hydrogen atom, $R^3$ is an alkyl group having from 1 to 8 carbon atoms or an aryl group, a has a value of less than or equal to 0.6, b has a value of zero or greater than zero, c has a value of greater than zero, d has a value of less than 0.5, the value of a+b+c+d=1, with the proviso that when each $R^8$ is methyl the value of b is less than 0.3, with the proviso that there are at least two silicon-bonded hydrogen atoms present in the silicone resin and with the proviso that greater than 10 wt % of the $R^7+R^8+R^3$ groups are phenyl; and (B') at least one non-aryl containing alcohol having the formula $CH_2$=$CH(CH_2)_xOH$, $CH_2$=$CHCH(CH_3)(CH_2)_xOH$, or $CH_2$=$C(CH_3)(CH_2)_xOH$ wherein x has a value of 1 to 10; in the presence of (C') a hydrosilylation catalyst; and optionally (D') at least one solvent.

9. The method of preparing carbinol-functional silicone resins according to claim 8 where a has a value of 0.1 to 0.6, b has a value of 0 to 0.4, c has a value of 0.3 to 0.8, and d has a value of 0 to 0.3.

10. The method of preparing carbinol-functional silicone resins according to claim 8 where the hydrogen-functional silicone resins of (A) are selected from hydrogen-functional silicone resins comprising the units:

$((CH_3)_3SiO_{1/2})_a$ $((H)CH_3SiO_{2/2})_b$ $((C_6H_5)CH_3SiO_{2/2})_b$ and $(C_6H_5SiO_{3/2})_c$, hydrogen-functional silicone resins comprising the units:

$((H)(CH_3)_2SiO_{1/2})_a$ $(C_6H_5SiO_{3/2})_c$, hydrogen-functional silicone resins comprising the units:

$((H)(CH_3)_2SiO_{1/2})_a$ $(CH_3SiO_{3/2})_c$, hydrogen-functional silicone resins comprising the units:

$((H)(CH_3)_2SiO_{1/2})_a$ $(CH_3SiO_{3/2})_c$ and $(C_6H_5SiO_{3/2})_c$, and hydrogen-functional silicone resins comprising the units:

$((CH_3)_3SiO_{1/2})_a$ $((H)(CH_3)_2SiO_{1/2})_a$ $(C_6H_5SiO_{3/2})_c$ wherein a has a value of 0.1 to 0.6, b has a value of 0 to 0.4, and c has a value of 0.3 to 0.8.

11. A method of preparing carbinol-functional silicone resins comprising reacting:

(A') at least one hydrogen-functional silicone resin comprising the units:

$(R^7_3SiO_{1/2})_a$ (i)

$(R^8_2SiO_{2/2})_b$ (ii)

$(R^3SiO_{3/2})_c$ (iii) and $(SiO_{4/2})_d$ (iv)

wherein $R^7$ and $R^8$ are each independently an alkyl group having from 1 to 8 carbon atoms, an aryl group, or a hydrogen atom, $R^3$ is an alkyl group having from 1 to 8 carbon atoms or an aryl group, a has a value of less than or equal to 0.6, b has a value of zero or greater than zero, c has a value of greater than zero, d has a value of less than 0.5, the value of a+b+c+d=1, with the proviso that when each $R^8$ is methyl the value of b is less than 0.3, with the proviso that there are at least two silicon-bonded hydrogen atoms present in the silicone resin and with the proviso that greater than 30 wt % of the $R^7+R^8+R^3$ groups are phenyl; and (B') at least one non-aryl containing alcohol having the formula $CH_2$=$CH(CH_2)_xOH$, $CH_2$=$CHCH(CH_3)(CH_2)_xOH$, or $CH_2$=$C(CH_3)(CH_2)_xOH$, wherein x has a value of 1 to 10; in the presence of (C') a hydrosilylation catalyst; and optionally (D') at least one solvent.

12. The method of preparing carbinol-functional silicone resins according to claim 11 where a has a value of 0.1 to 0.6, b has a value of 0 to 0.4, c has a value of 0.3 to 0.8, and d has a value of 0 to 0.3.

13. An emulsion composition comprising: (A) a carbinol-functional silicone resin comprising the units:

$(R^1{}_3SiO_{1/2})_a$ (i)

$(R^2{}_2SiO_{2/2})_b$ (ii)

$(R^3SiO_{3/2})_c$ (iii) and $(SiO_{4/2})_d$ (iv)

wherein $R^1$ and $R^2$ are each independently a hydrogen atom, an alkyl group having from 1 to 8 carbon atoms, an aryl group, a carbinol group free of aryl groups having at least 3 carbon atoms, or an aryl-containing carbinol group having at least 6 carbon atoms, $R^3$ is an alkyl group having from 1 to 8 carbon atoms or an aryl group, a has a value of less than or equal to 0.6, b has a value of zero or greater than zero, c has a value of greater than zero, d has a value of less than 0.5, and the value of a+b+c+d=1, and with the provisos that when each $R^2$ is methyl the value of b is less than 0.3, greater than 10 weight percent of the $R^1+R^2+R^3$ groups are phenyl, and there is on average at least one carbinol group per resin molecule; (B) at least one surfactant; and (C) water.

14. The emulsion composition according to claim 13 wherein
the alkyl group is methyl;
the aryl group is phenyl;
the carbinol group free of aryl groups having at least 3 carbon atoms is selected from a group having the formula $R^4OH$ wherein $R^4$ is selected from
(1) a group having the formula $—(CH_2)_x—$ where x has a value of 3 to 10,
(2) $—CH_2CH(CH_3)—$,
(3) $—CH_2CH(CH_3)CH_2—$,
(4) $—CH_2CH_2CH(CH_2CH_3)CH_2CH_2CH_2—$, and
(5) a group having the formula $—OCH(CH_3)(CH_2)_x—$ wherein x has a value of 1 to 10 and a group having the formula $R^6(OH)$ wherein $R^6$ is a group having the formula $—CH_2CH_2(CH_2)_xOCH_2CH—$ wherein x in each case has a value of 1 to 10;
the aryl-containing carbinol group having at least 6 carbon atoms is a group having the formula $R^5OH$ wherein $R^5$ is selected from
(1) a group having the formula $—(CH_2)_xC_6H_4—$ wherein x has a value of 0 to 10,
(2) a group having the formula $—CH_2CH(CH_3)(CH_2)_x$ $C_6H_4—$ wherein x has a value of 0 to 10, and
(3) a group having the formula $—(CH_2)_xC_6H_4(CH_2)_x—$ wherein x has a value of 1 to 10.

15. The emulsion composition according to claim 13 wherein where a has a value of 0.1 to 0.6, b has a value of 0 to 0.4, c has a value of 0.3 to 0.8, and d has a value of 0 to 0.3.

16. The emulsion composition according to claim 15 wherein the emulsion composition further comprises at least one ingredient selected from fragrances, preservatives, vitamins, ceramides, amino-acid derivatives, liposomes, polyols, botanicals, conditioning agents, glycols, vitamin A, vitamin C, vitamin E, Pro-Vitamin B5, sunscreen agents, humectants, preservatives, emollients, occlusive agents, esters, pigments, and self-tanning agents.

17. The emulsion composition according to claim 13 wherein the carbinol-functional silicone resin is selected from
carbinol-functional silicone resins comprising the units:

$((CH_3)_3SiO_{1/2})_a$ $((R^2)CH_3SiO_{2/2})_b$ where $R^2=—(CH_2)_3C_6H_4OH$ $((C_6H_5)CH_3SiO_{2/2})_b$ and $(C_6H_5SiO_{3/2})_c$, carbinol-functional silicone resins comprising the units:

$((R^1)(CH_3)_2SiO_{1/2})_a$ where $R^1=—(CH_2)_3C_6H_4OH$ and $(C_6H_5SiO_{3/2})_c$, carbinol-functional silicone resins comprising the units:

$((R^1)(CH_3)_2SiO_{1/2})_a$ where $R^1=—(CH_2)_3C_6H_4OH$ and $(CH_3SiO_{3/2})_c$, carbinol-functional silicone resins comprising the units:

$((R^1)(CH_3)_2SiO_{1/2})_a$ where $R^1=—(CH_2)_3OH$ and $(C_6H_5SiO_{3/2})_c$, carbinol-functional silicone resins comprising the units:

$((R^1)(CH_3)_2SiO_{1/2})_a$ where $R^1=—(CH_2)_3OH$ $(CH_3SiO_{3/2})_c$ and $(C_6H_5SiO_{3/2})_c$, carbinol-functional silicone resins comprising the units:

$((CH_3)_3SiO_{1/2})_a$ $((R^2)CH_3SiO_{2/2})_b$ where $R^2=—(CH_2)_3OH$ $((C_6H_5)CH_3SiO_{2/2})_b$ and $(C_6H_5SiO_{3/2})_c$, carbinol-functional silicone resins comprising the units:

$((CH_3)_3SiO_{1/2})_a$ $((R^1)(CH_3)_2SiO_{1/2})_a$ where $R^1=—(CH_2)_3OH$ and $(C_6H_5SiO_{3/2})_c$, carbinol-functional silicone resins comprising the units:

$((R^1)(CH_3)_2SiO_{1/2})_a$ where $R^1=—CH_2CH(CH_3)CH_2OH$ $((H)(CH_3)_2SiO_{1/2})_a$ and $(C_6H_5SiO_{3/2})_c$, carbinol-functional silicone resins comprising the units:

$((R^1)(CH_3)_2SiO_{1/2})_a$ where $R^1=—(CH_2)_3OH$ $(CH_3SiO_{3/2})_c$ wherein a has a value of 0.1 to 0.6, b has a value of zero to 0.4, and c has a value of 0.3 to 0.8.

18. The emulsion composition according to claim 13 wherein the emulsion composition further comprises at least one ingredient selected from fragrances, preservatives, vitamins, ceramides, amino-acid derivatives, liposomes, polyols, botanicals, conditioning agents, glycols, vitamin A, vitamin C, vitamin E, Pro-Vitamin B5, sunscreen agents, humectants, preservatives, emollients, occlusive agents, esters, pigments, and self-tanning agents.

19. The emulsion composition according to claim 13 wherein greater than 25 weight percent of the $R^1+R^2+R^3$ groups are phenyl.

* * * * *